US005893263A

United States Patent [19]
Matsumoto et al.

[11] Patent Number: 5,893,263
[45] Date of Patent: Apr. 13, 1999

[54] AUTOMATIC BAR CODE LABEL APPLYING APPARATUS FOR TEST TUBES

[75] Inventors: Toshikazu Matsumoto; Yoshimi Hirasawa, both of Kanagawa-ken, Japan

[73] Assignee: Techno Medica Co., Ltd., Kanagawa-Ken, Japan

[21] Appl. No.: 08/684,487

[22] Filed: Jul. 19, 1996

[51] Int. Cl.[6] ............... B65C 3/00; B65C 3/02
[52] U.S. Cl. .............. 156/387; 156/384; 156/556; 156/566; 156/569
[58] Field of Search ............... 156/556, 569, 156/384, 387, 277, 566, DIG. 11, DIG. 28

[56] References Cited

U.S. PATENT DOCUMENTS

| 4,534,465 | 8/1985 | Rothermel et al. | 422/104 X |
| 4,595,562 | 6/1986 | Liston et al. | 422/102 X |
| 4,609,017 | 9/1986 | Coulter et al. | 422/100 X |
| 5,688,361 | 11/1997 | Itoh | 156/362 |

FOREIGN PATENT DOCUMENTS

| 0642024 | 8/1995 | European Pat. Off. |
| 7132917 | 5/1995 | Japan |

Primary Examiner—Jeff H. Aftergut
Attorney, Agent, or Firm—Hardaway Law Firm P.A.

[57] ABSTRACT

An automatic bar code label applying apparatus is characterized by comprising at least a test tube containing section (1) for containing test tubes (11) of a same type to be applied with respective bar code labels, a collection device (2) for collecting the test tubes from the test tube containing section, a transfer device (3) for transferring the collected test tubes to a bar code label applying station (41), a printing/application device for printing characters and bar codes on the labels and applying the printed labels to the respective test tubes and a delivery device for delivering the test tubes with applied bar code labels.

8 Claims, 8 Drawing Sheets

CLOSURE

CLOSURE

5,893,263

AUTOMATIC BAR CODE LABEL APPLYING APPARATUS FOR TEST TUBES

BACKGROUND OF THE INVENTION

The present invention relates to an automatic bar code label applying apparatus to be suitably used for test tubes and blood sample tubes (hereinafter also referred to as test tubes) containing blood, body fluid or some other fluid constituting the object of a screening operation, the label to be applied typically carrying data on the fluid to be screened in the form of characters and a bar code.

In the operation of examining a blood sample in a hospital, the sample is typically examined for a number of test items and the type (size) of the test tube for containing the sample may be selected depending on the test items. A large amount of data may have to be carried by the test tube in order to identify the subject of medical examination and such data may typically include the name and the sex of the subject, the status of inpatient or outpatient and the department in charge of the patient. Recently, efforts have been paid to computerize the operation of controlling the entire hospital by means of either an on-line system or an off-line system and the use of bar code labels carrying thereon characters and bar codes for test tubes is of course in line with such efforts.

While the use of bar code labels for test tubes is advantageous because they can simplify the post-examination management and the accounting system of the hospital but is accompanied by a cumbersome task of applying them to the respective test tubes on a one by one basis. Grave consequences may arise if they happen to be applied to wrong test tubes by careless mistake. In view of these circumstances, there is a demand for the technology of automatically applying bar code labels to test tubes.

It is, therefore, an object of the present invention to provide an automatic bar code label applying apparatus to be suitably used for test tubes.

SUMMARY OF THE INVENTION

According to the present invention, the above object is achieved by providing an automatic bar code applying apparatus wherein it comprises least a test tube containing section for containing test tubes of a same type to be applied with respective bar code labels, a collection means for collecting the test tubes from the test tube containing section, a transfer means for transferring the collected test tubes to a bar code label applying station, a printing/application means for printing characters and bar codes on the labels and applying the printed labels to the respective test tubes, and a delivery means for delivering the test tubes with applied bar code labels.

The present invention will now be described in greater detail by referring to the accompanying drawings that illustrate a preferred embodiment of automatic bar code label applying apparatus according to the present invention.

DETAILED DESCRIPTION OF THE PREFERRED EMBODIMENT

Figure 1:
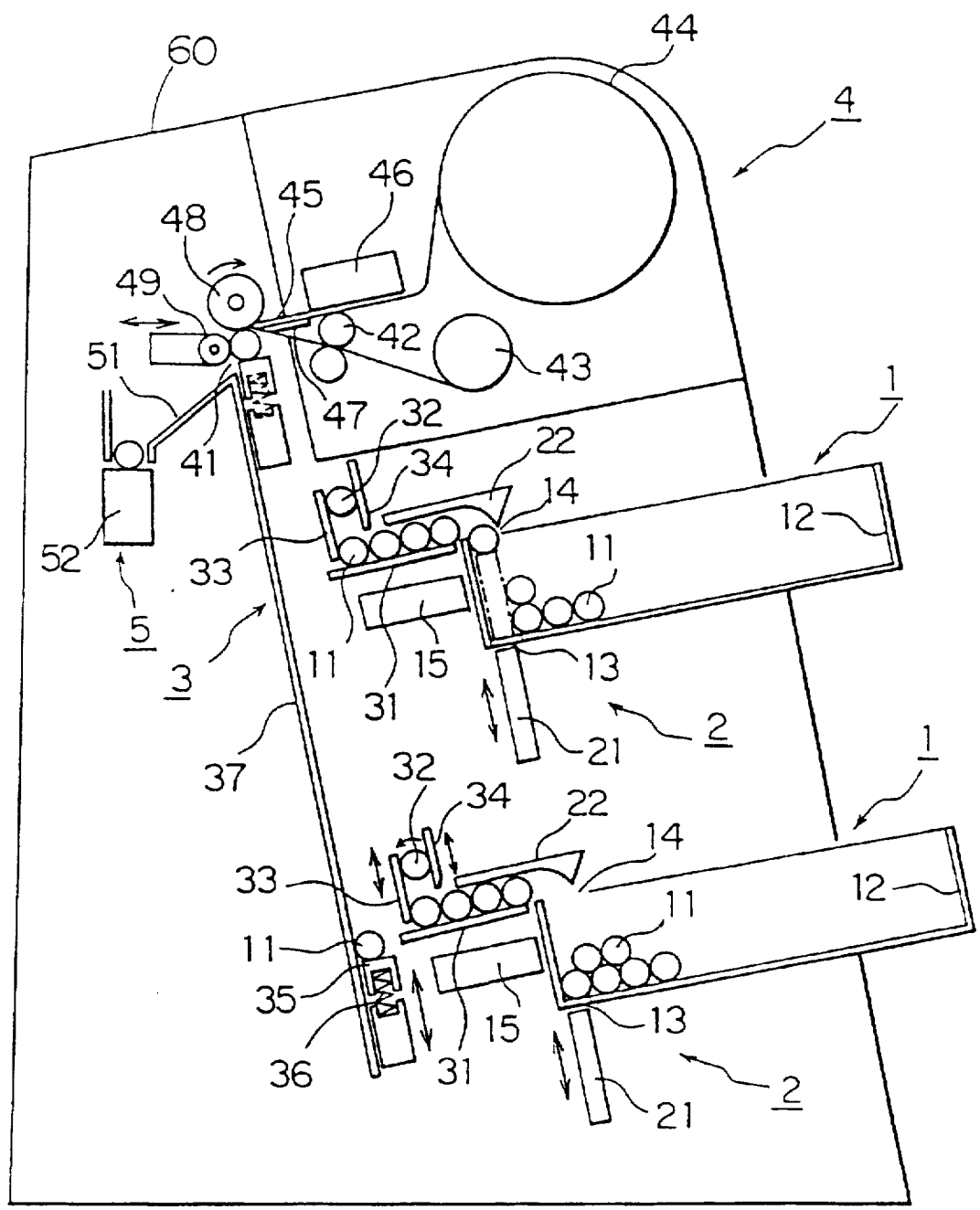
FIG. 1 is a schematic cross sectional view of an embodiment of an automatic bar code label applying apparatus for test tubes according to the present invention.

Referring firstly to FIG. 1, there is illustrated an embodiment of an automatic bar code label applying apparatus according to the present invention. It comprises a pair of test tube containing sections 1, a pair of collection means 2, transfer means 3, a printing/application means 4 and a delivery means 5. These components are contained in a casing 60. Test tubes 11 are handled in a substantially horizontal state in the casing 60 from the time when they are brought into the test tube containing section to the time when they are discharged from the delivery means 5. Since the members of each pair are identical relative to each other, they will be described hereinafter only in terms of either of them indiscriminately.

Figure 2:
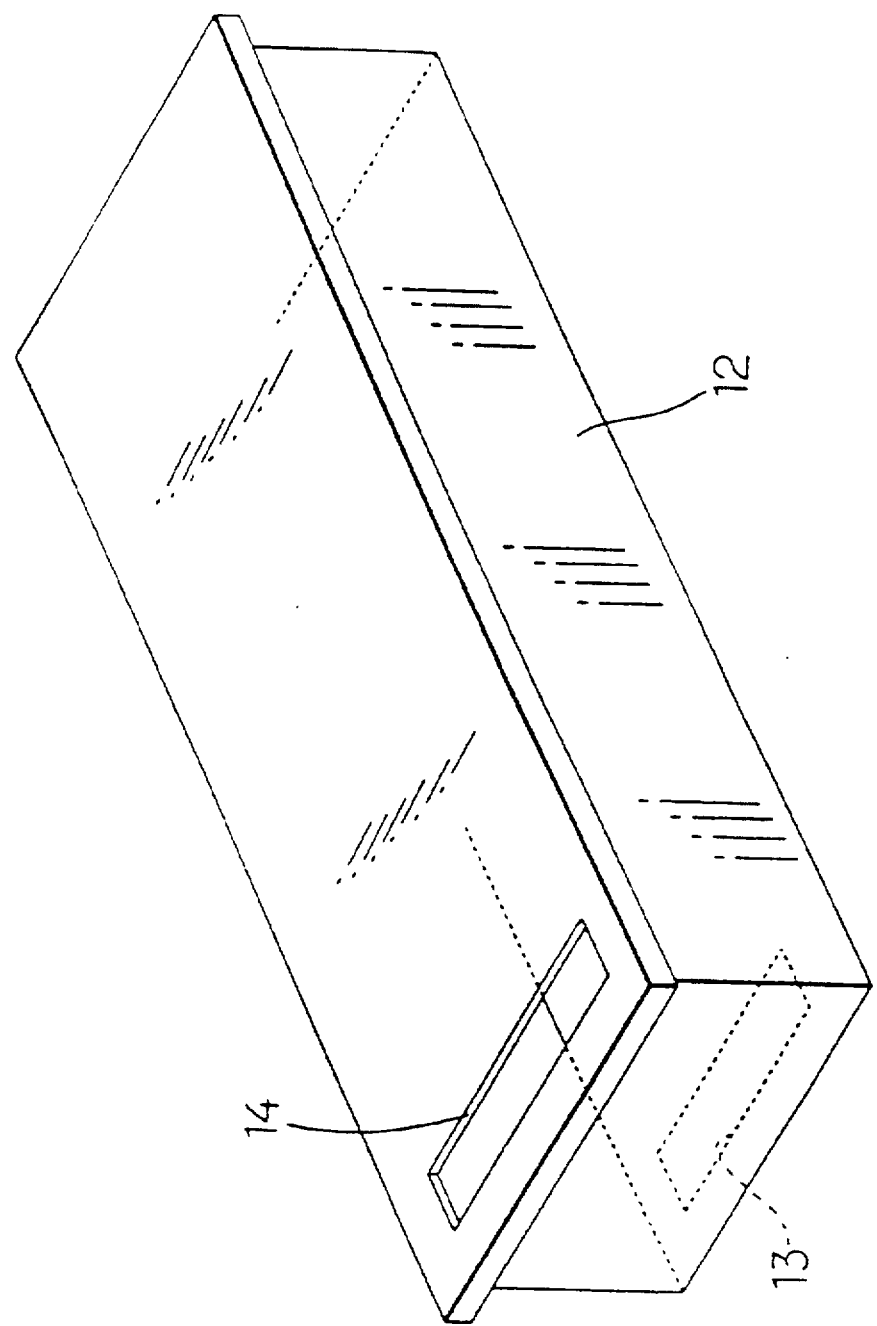
FIG. 2 is a schematic perspective view of a test tube case that can be used for the test tube containing section of the automatic bar code label applying apparatus according to the present invention.

Each of the test tube containing sections 1 includes a test tube case 12 which contains a number of test tubes 11 and is removably mounted on the casing 60. As shown in FIG. 2, each test tube case 12 may comprise a rectangular shaped box, and the bottom of each test tube case 12 is provided in an area located close to one of the longitudinal opposite ends with an opening 13 for receiving the collection means 2. Upper surface portion of each test tube case 12 may include an opening and shutting closure which is provided with at least in an area located vis-a-vis an opening 13 with a corresponding opening 14 for collecting test tubes. Each of the openings 13 is rectangular and dimensioned to be slightly smaller than the test tube 11. If each test tube case 12 comprises a conventional test tube case that can be purchased at any ordinary store selling medical equipments, such conventional test tube case may conveniently be perforated in a suitable portion of the bottom thereof at the time when it is manufactured, and then each opening 13 may be produced without difficulty by removing a rectangular strip from each test tube case 12 along the perforation. Each test tube collection opening 14 may also be produced by arranging a perforation on the closure at the time when it is manufactured. Alternatively, such opening may be produced simply by displacing or totally removing the closure. Each test tube case 12 provided with the openings 13 and 14 and containing test tubes therein is set in position in the casing 60 and slightly tilted toward the side adjacent to the openings 13 and 14 as shown in FIG. 1.

Figure 3:
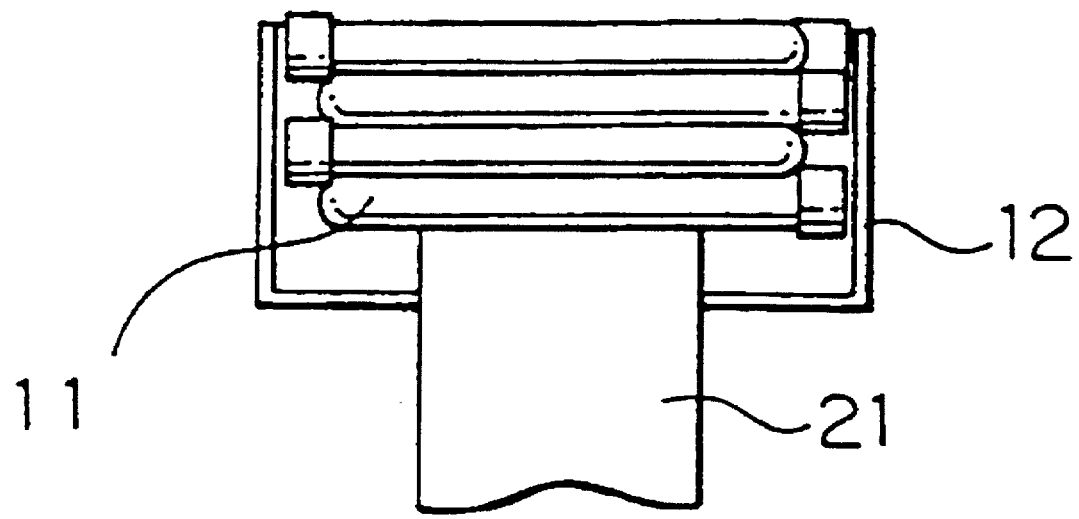
FIG. 3 is a schematic longitudinal sectional view of a test tube with a test tube pushing up member currently pushing up test tubes.

The collection means 2 is provided with a test tube pushing up means 21 having a length equal to the depth of the test tube case 12 so that the test tubes 11 in the case can be pushed up and collected on a row by row basis as the test tube pushing up means 21 is introduced into the case through the opening 13 (FIG. 3) and brought up so that all the test tubes 11 in the extreme row are pushed out of the test tube case 12 by a single action of the means 21. The pushed out test tubes 11 are directed appropriately by a guide member 22 and brought to a stand-by area 31 of the transfer means 3.

The test tube pushing up member 21 that has pushed out the test tubes of a row is then retracted out of the test tube case 12 so that the test tubes 11 remaining in the case 12 move downward by their own weight and the test tubes 11 of the extreme row come into contact with the side of the case 12 adjacent to the openings 13 and 14. Note that, if the test tubes in the case are covered by respective rubber caps, they can hardly slide and rotate to move downward in the case. Therefore, at least part of the inner surface of the case 12 (e.g., the oppositely disposed lateral sides and areas of the bottom along its longitudinal edges) is preferably coated with a slippery thin film to allow a sliding and rotating motion of the test tubes 11. Also note that the apparatus of FIG. 1 is provided with bar code readers 15 for reading the bar code of each of the test tubes contained in the cases arranged in position in the apparatus in order to ensure that test tubes of the right type are housed in the cases 12. Each of the bar code readers is arranged vis-a-vis the side of the corresponding case adjacent to the openings 13 and 14.

The foremost one of the test tubes 11 in the stand-by area 31 that are ready to be moved to the printing/application means 4 is fed onto a transfer table 35 as one of a pair of racks (33 in FIG. 1) is raised and the other (34 in FIG. 1) is lowered by the reciprocating rotary motion of a pinion 32 that is held in engagement with the racks 33 and 34 and the next one is moved to the foremost position of the stand-by area by the following rising/falling motion of the racks. The transfer table 35 preferably comprises upper and lower (front and rear) sections with a buffer spring 36 disposed therebetween.

The transfer table 35 carrying thereon a test tube is moved upward along a guide panel or a guide rail 37 up to a bar code label applying station 41 of the printing/application means 4 and held there until the operation of applying a bar code label to the test tube is completed. If the test tube secured in position by the transfer table 35 is the one 11a taken out from the lower case 12, the transfer table 35 is then moved to a position next to the upper stand-by area 31 of the transfer means 3, where it receives a test tube 11 from the upper case 12 and brings it to the bar code label applying station 41 so that another bar code label may be applied to the test tube 11 in a manner as described above. By repeating this operation, all the test tubes 11 that are contained in the respective cases 12 and may be of two different types are carried by the transfer table 35 and moved to the printing/application means 4 for application of respective bar code labels on a one by one basis.

The printing/application means 4 has a roller 42 operating both as a drive roller and as a platen, a web take-up roller 43 and a label carrying web feed roller 44, of which the web take-up roller rotates in synchronism with the roller 42 to take up the web from the feed roller 44 so that characters and a bar code are printed on the foremost label 45 according to the data transmitted from a computer. After the printing operation is over, the printed label 45 is peeled off from the web by a separator plate 48 that acutely changes the direction of advancement of the web and then applied to the test tube 11 that is rotating at the bar code label applying station 41 located at the front end of the separator plate 47. The transfer means 3 is provided with a sensor (not shown) for sensing the orientation of each test tube 11. This sensor may be disposed on the stand-by area 31 or the guide rail 37, and intended to detect the orientation of each test tube 11 before a bar code label is applied thereto by the printing/application means 4 and to feed an orientation signal to the printing/application means 4. In response to the received orientation signal the printing/application means 4 is operated to change or set the orientation of the printing to the bar code label to be applied. In this way, the bar code label can be applied to each test tube 11 so that a bar code may always have same orientation independent on the orientation of the test tubes which are contained in the test tube case 12.

The test tube 11 is made to rotate around its axis by a test tube drive roller 48 while it is waiting for an operation of bar code label printing/application. A pressing roller 49 reciprocating moves toward and away from the test tube to ensure that the test tube comes into contact with the rotary drive roller 48 and a label 45 is wound around the test tube.

Additionally, the pressing roller 49 prevents the test tube from being moved toward the delivery means when it approaches the test tube.

After the operation of applying a label 45 to the test tube is completed at the bar code label applying station 41, the pressing roller 49 is moved away from the test tube which is now carrying a bar code label and the test tube is then allowed to fall into a hopper 51 of the delivery means 5. At the bottom of the hopper, the test tube is received by a belt conveyor 52 moving perpendicular to the plane of FIG. 1.

The belt conveyor 52 is arranged to be extended between an inlet port 61 and an outlet port 62 provided on both sides of the casing and is operated to transfer the test tubes with the bar code label being applied from the outlet port to the outside.

Figure 4:
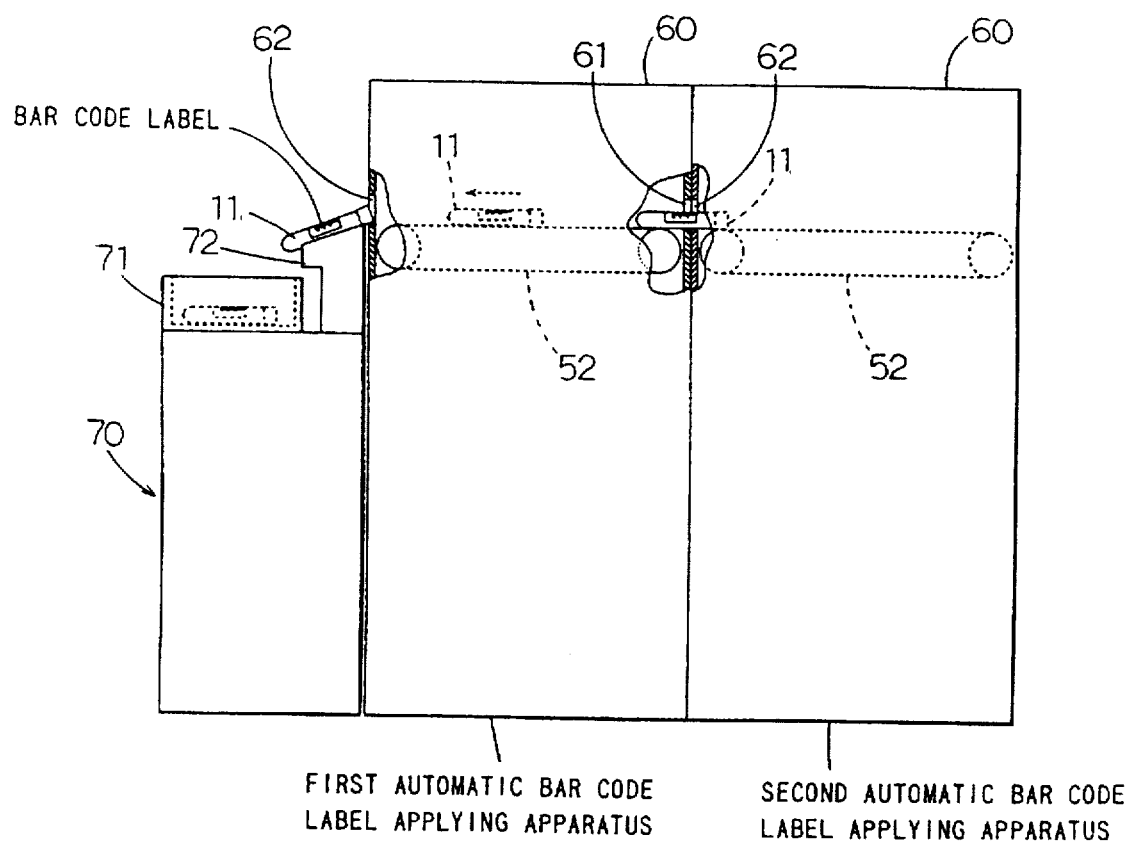
FIG. 4 is a schematic view showing an arrangement in which two automatic bar code label applying apparatuses are juxtaposed in such a manner that an outlet port of one of the apparatuses is aligned with an inlet port of the other apparatus.

A plurality of automatic bar code label applying apparatus thus constructed may be prepared and as shown in FIG. 4, may be juxtaposed in such a manner that the inlet and outlet ports of the adjacent apparatuses are aligned with each other and the belt conveyors 52 of the respective apparatuses are aligned with each other to form a single transfer channel. That is, the outlet port of the preceding unit is aligned with the inlet port of the succeeding unit and the belt conveyors 52 of the units are arranged on a single line to establish a single transportation route for test tubes, by means of which all the test tubes to which respective labels are applied in the units can be collected.

In FIG. 4 reference numeral 70 denotes a collector which includes test tube collecting boxes 71 and a guide member 72 and is disposed adjacent to the outlet port side of the first apparatus for receiving the test tubes each carrying a bar code label from the outlet port side of the first apparatus. Preferably, the test tube collector 70 may be arranged so that the test tubes carrying labels to which the same kind of bar code is printed are collected by the same collecting box 71.

Figure 5:
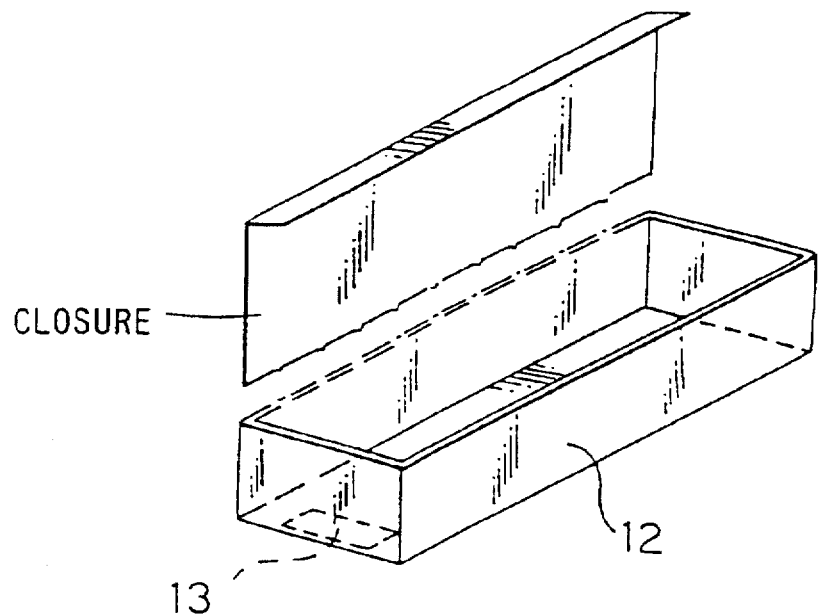
FIG. 5 is a schematic perspective view showing another test tube case that can be used for the test tube containing section of the automatic bar code label applying apparatus.
Figure 6:
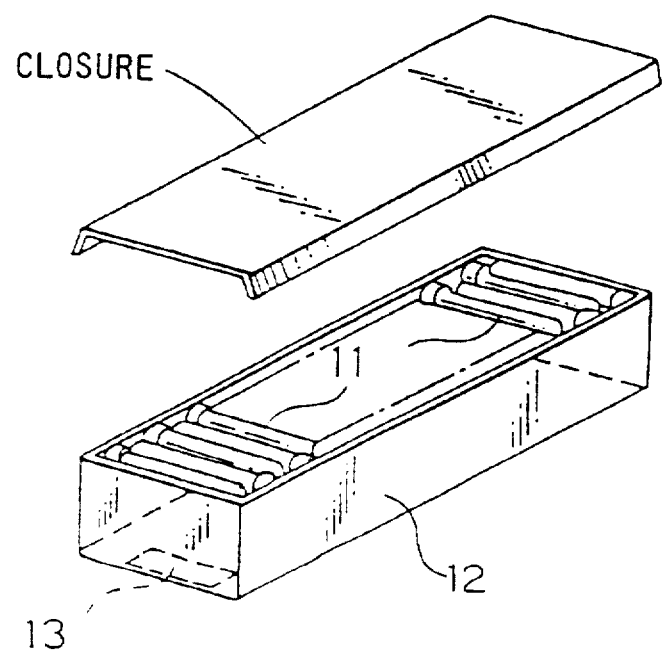
FIG. 6 is a schematic perspective view showing a further test tube case that can be used for the test tube containing section of an automatic bar code label applying apparatus.
Figure 7:
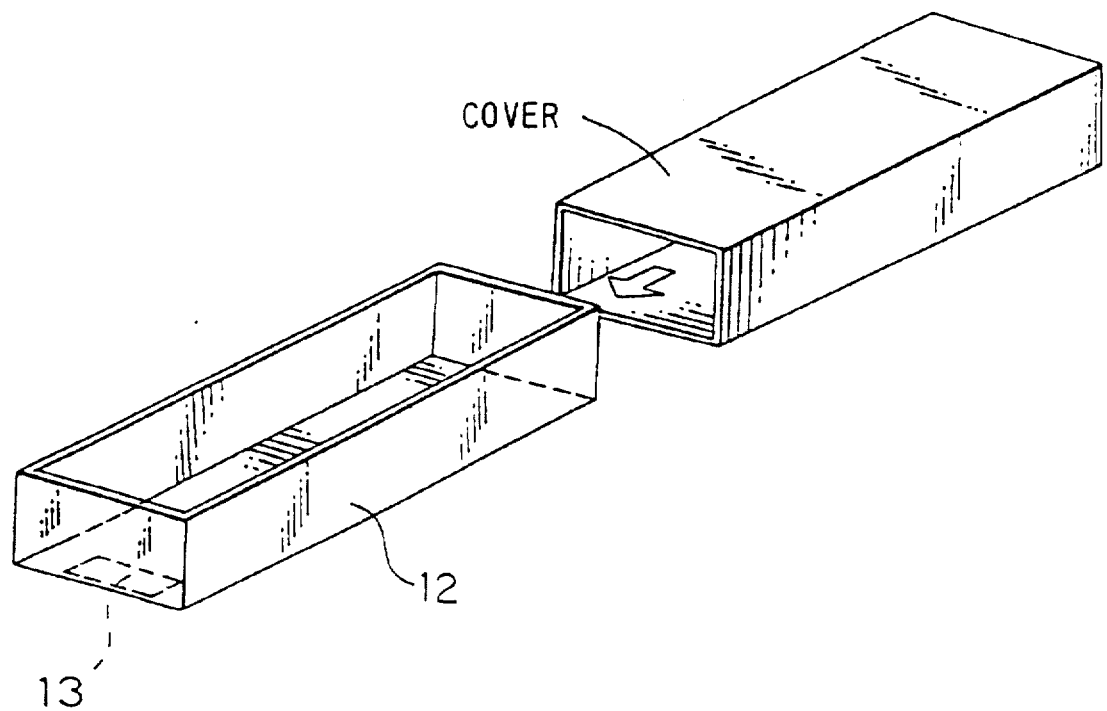
FIG. 7 is a schematic perspective view showing still another test tube case that can be used for the test tube containing section of an automatic bar code label applying apparatus.

FIGS. 5 through 7 illustrate different examples of the test tube case 12.

The test tube case illustrated in FIG. 5 has a bottom portion provided with an opening 13 for receiving the collection means 2 and an upper portion provided with a removable closure which is removed when the test tube case is mounted on the apparatus.

The test tube case illustrated in FIG. 6 is provided with a removable closure which is removed when the test tube case is mounted on the apparatus.

The test tube case illustrated in FIG. 7 is provided with a tubular cover. When this tube case is mounted on the apparatus the tubular cover is displaced so that the upper portion of the case is opened.

With the respective test tube cases thus constructed, it is unnecessary to provide an opening for collecting test tubes as in FIG. 2.

Figure 8:
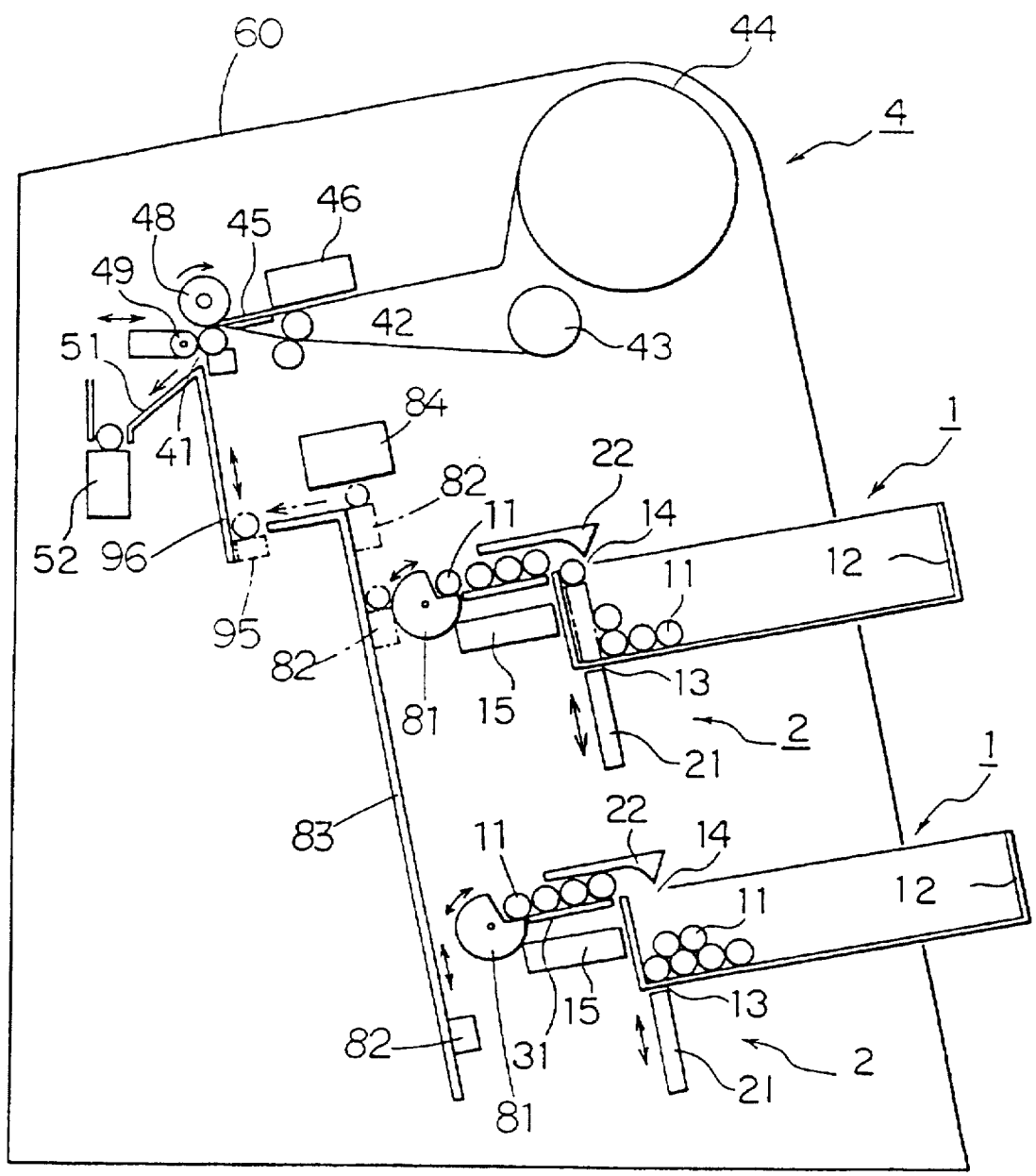
FIG. 8 is a schematic cross sectional view showing another embodiment of an automatic bar code label applying apparatus for test tubes according to the present invention.

FIG. 8 illustates another embodiment of the automatic bar code label applying apparatus which has the same essential components as ones in the embodiment of FIG. 1, the corresponding components being denoted by the same reference numerals as ones used in FIG. 1.

Figure 9:
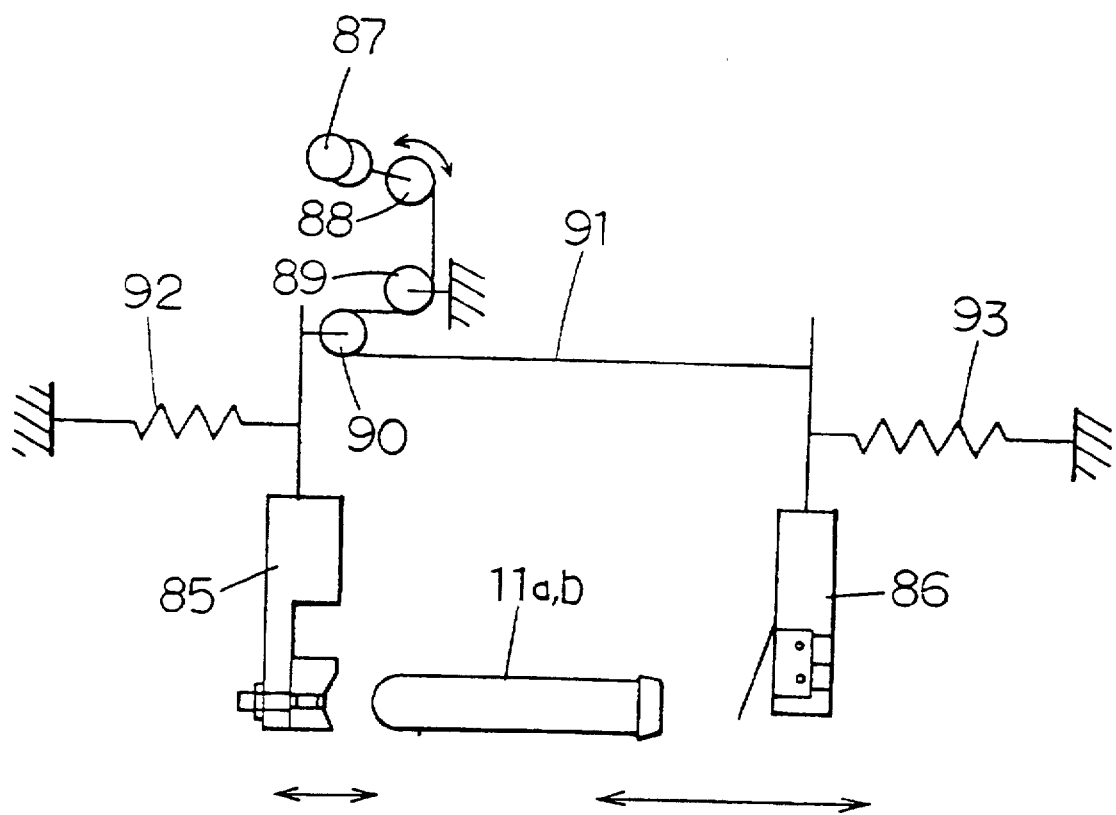
FIG. 9 is a schematic diagram showing a mechanism for sensing the orientation of each test tube.

Reference numeral 81 denotes a rotary tranfer means which is driven to transfer one by one the test tubes from the stand-by position 31 to a first tranfer table 82. The first tranfer table 82 is moved upward along a first guide rail 83 for transferring the test tubes 11 to an orientation detecting means 84. As shown in FIG. 9, this orientation detecting means 84 comprises a sensor 85 for sensing the forward end of each test tube and a sensor 86 for sensing the pressing of each test tube. When the test tube 11 lies between the sensors 85 and 86, a motor 87 actuated to drive pulleys 88, 98 and 90 and a wire 91 and thus the sensors 85 and 86 are moved opposite to each other for detecting the orientation of the test tube. After the the orientation of the test tube is detected, the motor 87 is reversely actuated so that the sensors 85 and 86 are returned to their orignal positions by means of springs 92 and 93. The orientation detecting means 84 feeds a detected orientation signal to the printing/application means 4 which in turn sets the direction of a printing based on the received orientation signal.

When a second transfer table 95 is moved downward, orientation detecting means 84 releases the test tube 11 to feed it on the second transfer table 95. Then, the second transfer table 95 is moved upward along a second guide rail 96 so as to feed the orientation detected test tube 11 to the bar code label applying station 41 of the printing/application means 4 and then test tube 11 is held at the bar code label applying station 41.

With the arrangement illustrated in FIG. 8 it is possible to attain an operating efficiency higher than the arrangement in FIG. 1 because the orientation detecting operation for one test tube can be performed by means of the orientation detecting means 84 while the applying operation of the bar code label for the other test tube is carried out by the printing/application means 4.

The test tube containing section 1 is not limited to the illustrated arrangement and may be so arranged that the test tube case may be integral with casing 60.

Additionally, while the above described embodiment of automatic bar code label applying apparatus comprises a pair of vertically arranged test tube containing sections 1, the arrangement and the number of test tube containing sections are not necessarily limited to the above embodiment and an automatic bar code label applying apparatus according to the invention may alternatively comprise a single test tube containing section 1 or three or more than three test tube containing sections. Still alternatively, if a plurality of test tube containing sections are used, they may be vertically or horizontally.

As described above in detail, with an automatic bar code applying apparatus according to the invention and comprising at least a test tube containing section (1) for containing test tubes (11) of a same type to be applied with respective bar code labels, a collection means (2) for collecting the test tubes from the test tube containing section, a transfer means (3) for transferring the collected test tubes to a bar code label applying station (41), a printing/application means for printing characters and bar codes on the labels and applying the printed labels to the respective test tubes and a delivery means for delivering the test tubes with applied bar code labels, the operation of applying labels to test tubes can be completely automated.

With the arrangement in which the test tube containing section is so arranged that a commercially available test tube case being used for distribution can be directly used for it, the test tubes in the case do not need to be moved into another case of the test tube containing section that is exclusively designed for it.

With the arrangement in which the test tube case is provided on the outer surface with a bar code, which is read at a position close to the test tube containing section, the risk of applying bar code labels to wrong test tubes can be practically eliminated.

With the arrangement in which at least part the inner surface of the test tube case is coated with a slippery thin film, test tubes provided with hardly slippery rubber caps can be easily and continuously taken out from the test tube containing section.

With the arrangement in which an automatic bar code label applying apparatus according to the invention comprises a plurality of test tube containing sections for a single printing/application means, labels can be applied to test tubes of different types or a large number of test tube of a same type in a same and single apparatus.

With the arrangement in which an automatic bar code label applying apparatus according to the invention is provided with a sensor for sensing the orientation of each test tube being fed to the printing/application means, characters and a bar code may be printed reversely on the label carried by each test tube arriving in a reversely oriented state so that the test tubes to be handled with this apparatus do not have to be arranged in advance for a same and single orientation. With such an arrangement, the apparatus can be structurally simplified.

We claim:

1. An automatic bar code applying apparatus comprising:
   at least one test tube containing section for containing test tubes of a same type to be applied with respective bar code labels;
   a printing/application means for printing characters and bar codes on the labels and applying the labels thus printed to the respective test tubes, said printing/application means and said at least one test tube containing section being in a superposed relationship;
   a collection means for collecting the test tubes from the respective test tube containing section;
   a transfer means for transferring the collected test tubes collected by the collection means to a bar code label applying station, said collection means and said transfer means being provided between said test tube containing section and said printing/application means; and
   a delivery means substantially horizontally arranged for delivering the test tubes with applied bar code labels.

2. An automatic bar code label applying apparatus according to claim 1, wherein said test tube containing section is so arranged that a supply of test tubes is directly fitted to it, said supply including a test tube case.

3. An automatic bar code label applying apparatus according to claim 2, wherein a bottom of said test tube case is provided in an area located close to one of a longitudinal opposite ends with an opening for receiving a test tube pushing member and the closure of the case is provided in an area located vis-a-vis the opening with a corresponding opening for collecting test tubes.

4. An automatic bar code label applying apparatus according to claim 3, wherein said test tube collection means includes a test tube pushing up member to be inserted into the test tube case through said opening for receiving a test tube pushing up member.

5. An automatic bar code label applying apparatus according to claim 4, wherein said test tube containing section is provided at a position close to the test tube case with a bar code reader for reading the bar code on the test tube case indicating a type of test tube it contains.

6. An automatic bar code label applying apparatus according to claim 5, wherein at least part the inner surface of the test tube case is coated with a slippery thin film.

7. An automatic bar code label applying apparatus according to claim 6, wherein a plurality of test tube containing sections are provided.

8. An automatic bar code label applying apparatus according to claim 7, wherein a sensor is provided for sensing an orientation of each test tube being fed to the printing/application means so that characters and a bar code may be printed reversely on the label carried by each test tube arriving in a reversely oriented state.

* * * * *